(12) United States Patent
Kusens et al.

(10) Patent No.: US 10,650,117 B2
(45) Date of Patent: *May 12, 2020

(54) METHODS AND SYSTEMS FOR AUDIO CALL DETECTION

(71) Applicant: CERNER INNOVATION, INC., Kansas City, KS (US)

(72) Inventors: Michael Kusens, Cooper City, FL (US); Neil Kusens, Sherman Oaks, CA (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,113

(22) Filed: Aug. 1, 2019

(65) Prior Publication Data

US 2019/0355475 A1 Nov. 21, 2019

Related U.S. Application Data

(63) Continuation of application No. 15/391,095, filed on Dec. 27, 2016.

(Continued)

(51) Int. Cl.
*G08B 23/00* (2006.01)
*G06F 19/00* (2018.01)
(Continued)

(52) U.S. Cl.
CPC ..... *G06F 19/3418* (2013.01); *G06K 9/00342* (2013.01); *G06K 9/00771* (2013.01);
(Continued)

(58) Field of Classification Search
CPC ... G16H 50/30; G10L 17/00; G10L 2015/088; G06K 9/00342; G06K 9/00771; G08B 21/0461; G08B 21/02
See application file for complete search history.

(56) References Cited

U.S. PATENT DOCUMENTS

| | | |
|---|---|---|
| 6,804,656 B1 | 10/2004 | Rosenfeld et al. |
| 7,945,457 B2 | 5/2011 | Zaleski |

(Continued)

FOREIGN PATENT DOCUMENTS

| | | |
|---|---|---|
| WO | 2016/126845 A1 | 8/2016 |
| WO | 2017/058991 A1 | 4/2017 |
| WO | 2017/124056 A1 | 7/2017 |

OTHER PUBLICATIONS

Final Office Action received for U.S. Appl. No. 15/391,095, dated Aug. 29, 2018, 29 pages.

(Continued)

*Primary Examiner* — Dhaval V Patel
(74) *Attorney, Agent, or Firm* — Shook, Hardy & Bacon LLP

(57) ABSTRACT

Systems and methods allow caregivers, central monitoring, and/or other persons to monitor whether a patient or another person has generated a call, such as an audio call. The systems and methods work by detecting audio within one or more audio detection zones, which are predefined areas surrounding the patient or other person to be monitored. The systems and methods detect when a command/keyword is spoken in the audio detection zone and generate an appropriate alert to an appropriate role.

17 Claims, 12 Drawing Sheets

Related U.S. Application Data

(60) Provisional application No. 62/273,565, filed on Dec. 31, 2015.

(51) Int. Cl.

| | | |
|---|---|---|
| *G08B 21/02* | (2006.01) | |
| *G06K 9/00* | (2006.01) | |
| *G16H 40/67* | (2018.01) | |
| *G08B 21/04* | (2006.01) | |
| *G10L 17/00* | (2013.01) | |
| *G16H 50/30* | (2018.01) | |
| *G10L 15/08* | (2006.01) | |

(52) U.S. Cl.
CPC ......... *G08B 21/02* (2013.01); *G08B 21/0461* (2013.01); *G10L 17/00* (2013.01); *G16H 40/67* (2018.01); *G16H 50/30* (2018.01); *G10L 2015/088* (2013.01)

(56) References Cited

U.S. PATENT DOCUMENTS

| | | |
|---|---|---|
| 8,273,018 B1 | 9/2012 | Fackler et al. |
| 8,565,500 B2 | 10/2013 | Neff |
| 8,620,682 B2 | 12/2013 | Bechtel et al. |
| 8,769,153 B2 | 7/2014 | Dziubinski |
| 8,902,068 B2* | 12/2014 | Bechtel ................ A61M 5/142 340/573.1 |
| 8,917,186 B1 | 12/2014 | Grant |
| 9,424,699 B2 | 8/2016 | Kusens et al. |
| 9,466,163 B2 | 10/2016 | Kusens et al. |
| 9,538,158 B1 | 1/2017 | Rush et al. |
| 9,691,206 B2 | 6/2017 | Kusens et al. |
| 9,774,991 B2 | 9/2017 | Kusens |
| 9,838,849 B2 | 12/2017 | Kusens |
| 9,858,741 B2 | 1/2018 | Kusens et al. |
| 9,984,521 B1 | 5/2018 | Kusens et al. |
| 9,997,001 B2 | 6/2018 | Kusens et al. |
| 9,998,857 B2 | 6/2018 | Kusens |
| 10,013,831 B1 | 7/2018 | Kusens et al. |
| 10,109,179 B2 | 10/2018 | Kusens |
| 10,115,253 B2 | 10/2018 | Kusens et al. |
| 10,115,254 B1 | 10/2018 | Kusens et al. |
| 10,121,299 B2 | 11/2018 | Kusens et al. |
| 2008/0021709 A1 | 1/2008 | Greer |
| 2009/0278934 A1 | 11/2009 | Ecker et al. |
| 2011/0087079 A1* | 4/2011 | Aarts .................. A61B 7/003 600/300 |
| 2012/0140068 A1 | 6/2012 | Monroe et al. |
| 2012/0154582 A1 | 6/2012 | Johnson et al. |
| 2014/0365242 A1 | 12/2014 | Neff |
| 2016/0098676 A1 | 4/2016 | Kusens et al. |
| 2016/0267327 A1* | 9/2016 | Franz .................. A61B 5/1113 |
| 2017/0193180 A1 | 7/2017 | Kusens et al. |

OTHER PUBLICATIONS

Non-Final Office Action received for U.S. Appl. No. 15/391,095, dated Jan. 24, 2018, 13 pages.

Notice of Allowance received for U.S. Appl. No. 15/391,095., dated May 1, 2019, 10 pages.

Preinterview First Office Action received for U.S. Appl. No. 15/391,095 , dated Aug. 21, 2017, 4 pages.

\* cited by examiner

METHODS AND SYSTEMS FOR AUDIO CALL DETECTION

CROSS-REFERENCE TO RELATED APPLICATION

This application claims the benefit of U.S. Non-Provisional patent application Ser. No. 15/391,095, filed Dec. 27, 2016, entitled "Methods And Systems For Audio Call Detection", which claims priority to U.S. Provisional Patent Application No. 62/273,565, filed Dec. 31, 2015, entitled "Methods And Systems For Audio Call Detection," the disclosures of which are incorporated herein by reference in their entirety.

TECHNICAL FIELD

The present disclosure relates to methods and systems for detecting an audio call in a focused zone.

BACKGROUND

Traditionally, monitoring of healthcare patients is a costly, time-consuming endeavor. One of the tasks that require a large chunk of time is identifying patient calls for help or assistance or patient requests and responding to those calls. Typically, patients are equipped with a "call button" where they press the button and a call is generated to an assigned caregiver, regardless of the subject of the call. For example, a request for a snack (as all other requests) would be routed to the assigned nurse, for instance, rather than directly to the cafeteria. To be notified of calls, clinicians or any person that responds to calls are equipped with physical devices to receive the calls (e.g., pagers, mobile electronic devices, etc.). Furthermore, the responding party is blindly responding to a generic call since most calls are submitted in the same fashion: pressing the call button. There is not currently a system that eliminates the physical requirements of call-receiving devices while also adding specificity to calls and direct routing to appropriate roles.

SUMMARY

This brief summary is provided as a general overview of the more detailed disclosure which follows. It is not intended to identify key or essential elements of the disclosure, or to define the claim terms in isolation from the remainder of the disclosure, including the drawings.

This disclosure generally relates to systems and methods for detecting calls in a monitored zone. Generally, and without limitation, the method involves monitoring one or more focused areas (audio detection zone(s)) surrounding a subject(s) and filtering out audio detected anywhere besides the focus area(s). The method may comprise electronically receiving 2D or 3D motion and sound sensor data from one or more sensors positioned in a room with a patient. The motion data may be used to identify the position of the patient in the room. An audio detection zone may be defined around the patient, caregiver, or the like. Any areas in the monitored environment that are outside of the audio detection zone may be designated as audio ignore zones, where audio detected in those zones is ignored or not identified at all.

In some aspects, the method may comprise providing a warning or alert if an audio call is detected within the audio detection zone. An audio call, as used herein, refers generally to spoken phrases, keywords, or commands. An alert may be generated when phrases, keywords, or commands are detected in the audio detection zone.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The present disclosure is described in detail below with reference to the attached drawing figures, wherein.

DETAILED DESCRIPTION

Figure 1:
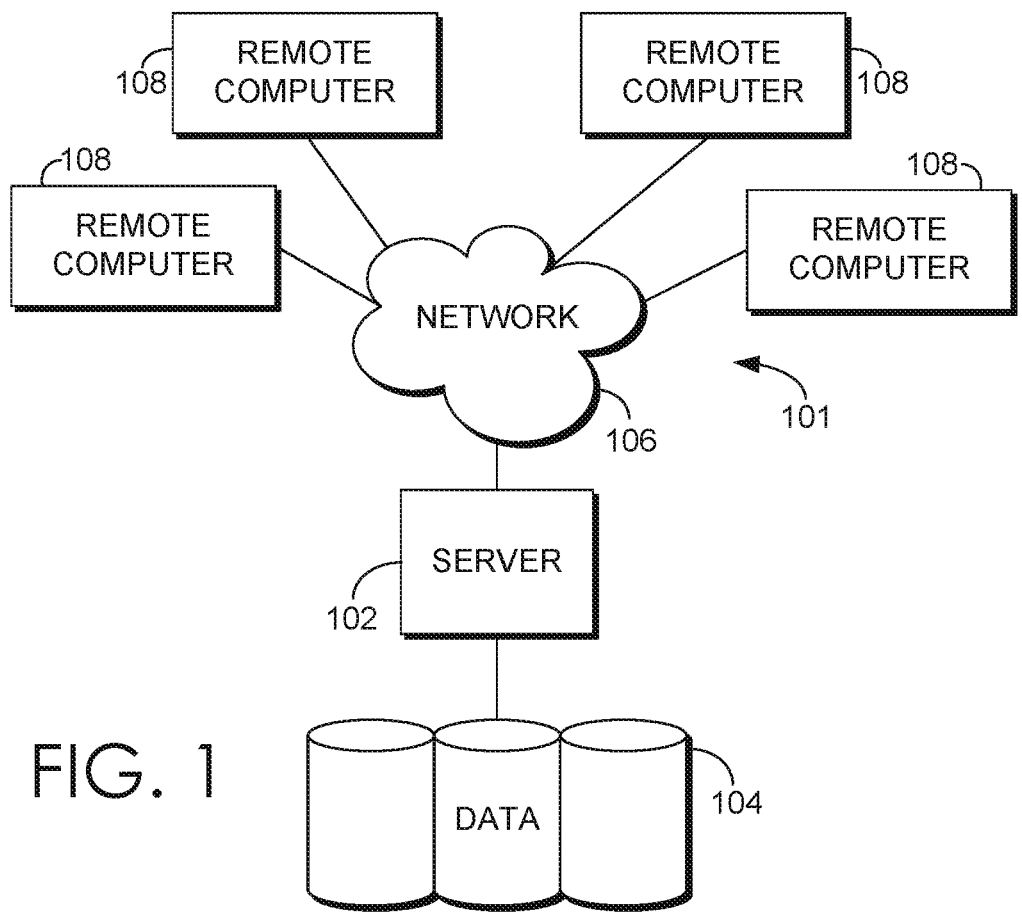
FIG. 1 is an exemplary environment to carry out embodiments of the present invention.

The present invention is directed to detection of audio calls. The detection described herein is performed using a camera equipped with motion and/or sound sensors ("the system"). The sound sensors are beneficial as some audio calls may be detected using the sound sensors. The system may be installed in any location where monitoring is desired. Specifically, the system may be installed where persons to be monitored are located (e.g., patient rooms). By installing the system that communicates with, for example, clinical workstations already present in a facility, the physical call-receiving devices may be eliminated. The monitoring system described herein can replace the physical call-devices presently used.

Additionally, the system can intelligently identify phrases, keywords, and commands so that the traditional generic nature of calls is limited. For example, the system can identify phrases such as "I need help getting up" or "I need a snack" and provide that in an alert so that a responding party is prepared to respond. Furthermore, the call may be intelligently routed to an appropriate role so that clinicians are not overwhelmed with irrelevant calls. For instance, a call that indicates "I need a snack" could be directly routed to the cafeteria so that a snack is brought up to the patient's room. A call for "a blanket" could be directly routed to supplies and a blanket could be delivered. This would reduce the number of calls sent to clinicians that aren't fulfilled by clinicians anyway. This would also provide more efficient responses to calls since the receiving party would be aware of the request prior to visiting the patient's room so that, in some cases, the responder could simply fulfill the request rather than visit the patient to inquire as to the request and leaving to fulfill the request in a subsequent visit. The system may also work with a patient's electronic health record (EHR) to ensure that requests are not fulfilled that conflict with a patient record. For example, a patient that requests a snack may be routed to a clinician rather than the cafeteria if the patient's record indicates that no food is to be administered to the patient.

There is also a need for systems, methods, and media that can help a caregiver or a supervisor of a caregiver monitor patients without unnecessary noise. Without a focused area or designated audio detection zones the result would be incredibly noisy and difficult to parse through. A focused audio detection zone eliminates unnecessary noise and only picks up on what is in focus (e.g., a patient, a caregiver, etc.). Additionally, phrases, commands, and keywords may be configured into a system such that only identified phrases, commands, and keywords are picked up in the audio detection zones.

In general, and as described in greater detail below, motion and sound sensors may be used to observe when a patient moves or speaks. The sensors may assess what words are spoken by a patient (or any other target) and not others outside of an audio detection zone. Motion sensors may also detect when a patient is speaking or when a patient is moving in a way that indicates a call for help.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 101. The computing environment 101 is merely an example of one suitable computing environment and is not intended to suggest any limitation as to the scope of use or functionality of the invention. Neither should the computing environment 101 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 101 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants, mobile phones, cameras, or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
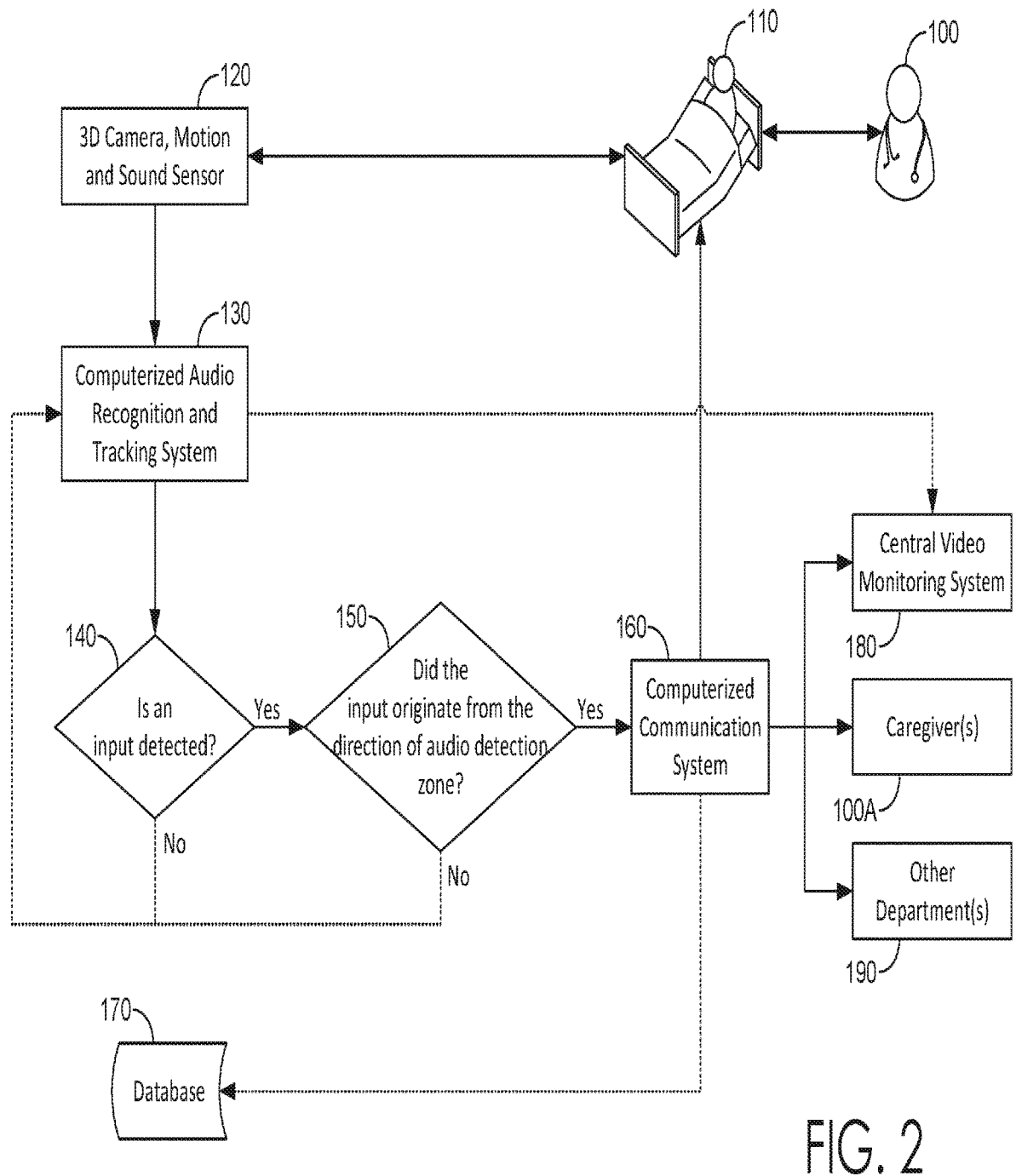
FIG. 2 is an exemplary flowchart for an audio call detection system.
Figure 3:
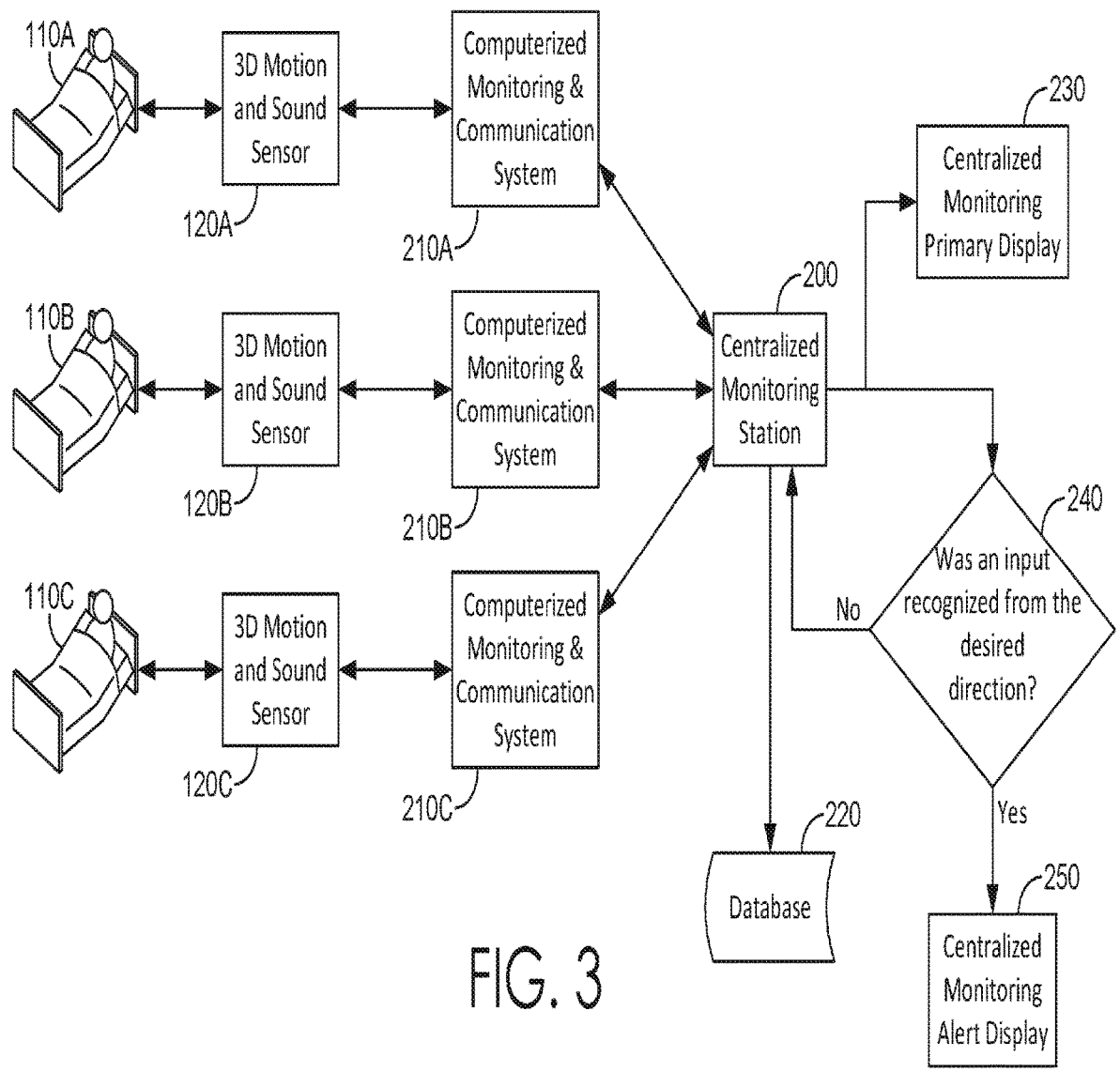
FIG. 3 is an exemplary flowchart for a central monitoring station for an audio call detection system.

Turning now to FIG. 2, an exemplary workflow is illustrated for monitoring motion and sound of a patient 110 (or other target) for alerting clinicians 100. In general, motion and/or sound sensors 120 are electronic devices that contain one or more cameras and one or more microphones, capable of identifying individual objects, people, and motion, regardless of lighting conditions. The motion and/or sound sensor may further contain one or more microphones to detect audio. As used herein, unless expressly described as an array of two or more sensors, reference to a sensor or sensors encompasses the singular and the plural, e.g., a singular sensor or an array of sensors, and an array of sensors may be physically housed in a unitary structure or may be physically distinct devices. The cameras may utilize technologies including, but not limited to, color RGB, CMOS sensors, lasers, infrared projectors and RF-modulated light. The motion and/or sound sensors 120 may contain one or more microprocessors and/or image sensors to detect and process information both transmitted and received by the sensor(s). Suitable 3D sensors can perceive depth, in contrast to 2D cameras which perceive only lateral and longitudinal positions, but both may be utilized in the present invention. Exemplary 3D motion sensors include the Microsoft® Kinect® Camera, the Sony® PlayStation® Camera and the Intel® RealSense™ Camera, each of which includes microphones for the audio detection aspect of the invention.

The motion and/or sound sensor 120 may be co-located with a person 110 to be monitored. The monitoring may occur in a variety of environments including, without limitation, a hospital, a home, a hospice care facility, a nursing home, an assisted living facility, an outpatient medical facility, and the like. The motion and/or sound sensor 120 may be positioned where it is likely to capture movements of a patient and/or audio spoken by the patient. For example, the motion and/or sound sensor 120 may be oriented to take images of a bed, chair, or other location where the patient 110 may spend a significant amount of time. The motion and/or sound sensor 120 may be permanently installed, or may be temporarily set up in a room as needed. The motion sensors 120 may be continuously on, intermittently on (e.g., may sample data for a second person in the room with the patient at fixed intervals), activated by motion or sound in the room, or manually activated, e.g., by the caregiver 100.

The motion and/or sound sensor 120 may communicate data, such as audio of the person being monitored, to a computerized audio recognition and tracking system 130. The computerized audio recognition and tracking system 130 may be a computer programmed to monitor transmissions of data from the sensor 120. The computerized audio recognition and tracking system 130 may be integral to the motion and/or sound sensor 120 or a distinctly separate apparatus from the motion and/or sound sensor 120, possibly in a remote location from motion and/or sound sensor 120 provided that the computerized audio recognition and tracking system 130 can receive data from the motion and/or sound sensor 120. The computerized audio recognition and tracking system 130 may be located in the monitored patient's room or the patient's location. The computerized audio recognition and tracking system 130 may be connected to a central video monitoring system 180. The computerized audio recognition and tracking system 130 and the central video monitoring system 180 may be remotely located at any physical location so long as a data connection exists (e.g., USB, TCP/IP, or comparable) between the central video monitoring system 180, the computerized communication system 160 (if separate from computerized video monitoring system 180), the central video monitoring system 180, and the motion and/or sound sensor 120.

Figure 4:
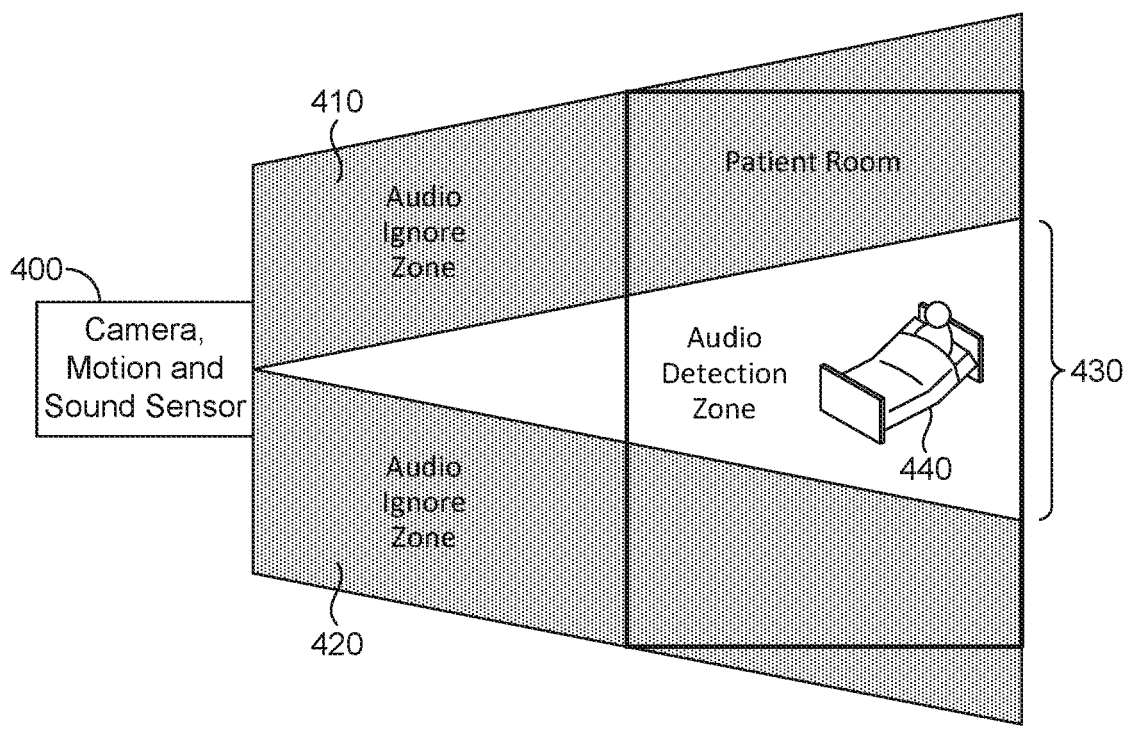
FIG. 4 is a diagram illustrating an audio detection zone.

The computerized audio recognition and tracking system 130 may receive data from motion and/or sound sensor 120. The data may include audio from one or more monitored zones or an audio detection zone(s) 430, as shown in FIG. 4. At step 140, the computerized audio recognition and tracking system 130 may assess whether an input including a command/keyword or phrase is detected in the monitored zone. Phrases, commands, and keywords may be configured by system owners, other users, etc. Any number of words or variations of words may be configured within the system as commands/keywords. For instance, the word "help" may be programmed in as a keyword along with "helllllp," which may be what is detected when a patient is yelling or moaning and stretching out the word "help." Any unrecognized words may be communicated to a centralized command center for further review and added to the system, if desired.

If a phrase or command/keyword is not detected, the computerized audio recognition and tracking system 130 may continue to monitor the area as long as the motion and/or sound sensor 120 continue to transmit data. If a phrase or command/keyword is detected within the monitored zone at step 140, the computerized audio recognition and tracking system 130 may determine, at step 150, if the phrase or command/keyword originated from the direction of the audio detection zone 430. If not, the computerized audio recognition and tracking system 130 may continue to monitor the area as long as the motion and/or sound sensor 120 continue to transmit data. If yes, the data is communicated to a computerized communication system 160 which, in turn, communicates the data to one or more of the central video monitoring system 180, the caregiver(s) 100A, or other departments 190. The data may be communicated on in the form of an alert when specific phrases or commands/keywords are detected within the audio detection zone 430. The data may also be communicated for informational purposes, to generate tasks, to request items, etc.

In addition to recognizing the inputs of phrases, commands, or keywords, the system 130 may further filter identified inputs based on additional criteria. Volume, for instance, may be used to aid in differentiation between normal conversation and a true emergency. A volume threshold, such as a predetermined decibel level, may be used as a trigger in conjunction with the phrases/commands/keywords. For instance, if an individual is yelling "help" at a volume level above the threshold (or above the predetermined decibel level) then the system 130 may identify that as a trigger to generate an alert, task, etc. However, if the individual says a keyword such as "help" in a normal course of conversation (e.g., "The staff is great; whenever I need help someone is here") the system 130 may not identify the keyword as a trigger if it is not above a predetermined volume threshold (using any sort of volume indicator desired).

The computerized audio recognition and tracking system 130 may be further configured to perform voice recognition on audio identified by the motion and/or sound sensor 120. The voice recognition may be programmed to only identify the voice of, for instance, the person 110 being monitored (e.g., identify the patient's voice rather than the patient's mother).

In embodiments, when an alert is triggered, the alert may be sent, at least initially, to the person 110 being monitored, to give the person 110 an opportunity to respond before alerting the central video monitoring system 180 and/or caregiver(s) 100. For example, an audible message may be played in the room where person 110 is being monitored, possibly asking something like, "Are you ok?" or "Do you need help?" The system can analyze data from motion and/or sound sensor 120 for gestures in addition to audio, such as a head nod, consistent with a yes or no answer. The motion and/or sound sensor 120 can also analyze sound data for recognizable words, such as yes, no, help, or even certain extended sounds, such as "oooooohhhhhhhhhh," which might be consistent with moaning or other vocalization associated with pain, discomfort, or disorientation. The central video monitoring system 180 may be alerted if no response is received or if the response is unintelligible or indicates that the person 110 being monitored wants or needs assistance. On receiving the alert, the central video monitoring system 180, or an attendant there, may view live image, video, and/or audio feed from the motion and/or sound sensor 120, and evaluate whether the audio detected is concerning or requires attention. Additionally, one or more caregiver(s) 100 may be alerted with or even before person 110 and/or central video monitoring system 180, so that the caregiver(s) 100 can assess what is happening with the person 110. Alternatively, the person 110, the caregiver(s), and the central video monitoring system 180 may be alerted at the same time. The priority and timing of alerts to different individuals or stations can be configured in accordance with the needs and desires of a particular facility, experience with a particular monitored individual or type of patient, or any other criterion of the system owner or user. The priority and timing of alerts to different individuals may be different for initial, continuing, and/or repeated alerts and may vary depending on the patient 110.

Data associated with alerts may be logged by computerized communication system 160, at least, in a database 170. Data associated with alerts may include, without limitation, the video and/or audio data from motion and/or sound sensor 120 that triggered the alert; buffered data preceding the video and/or audio data that triggered the alert; video and/or audio data subsequent to the alert; the individual(s) to whom an alert was addressed; the response, if any, receive or observed following an alert; and combinations thereof.

The present system can distinguish between alarms around a patient (e.g., IV pump alarms, heart monitor alarms, etc.) and identify severity between the alarms. For instance, the system is able to identify that an IV pump is going off as the bag needs to be replaced and automatically route an alert indicating such to the appropriate destination (e.g., the nurse that will replace the bag). Various devices may be identified within audio detection zones so that inputs from the devices are identified by the system. Alternatively, the devices in the room may be identified as being within the audio ignore zones but still be processed by the system.

As shown in FIG. 2, central monitoring station 200 may receive data from multiple computerized monitoring systems, 210A, 210B, and 210C. For simplicity, the computerized communication system associated with each computerized monitoring system is shown as an integrated component of the computerized monitoring system. If desired, separate computerized communication systems and/or a shared computerized communication system could be used. Computerized monitoring systems 210A, 210B, and 210C receive data from motion and/or sound sensors 120A, 120B, and 120C, which are, respectively, monitoring persons 110A, 110B, and 110C. Data received by the central monitoring station 2000 from computerized monitoring systems 210A, 210B, and 210C may routinely be displayed on central monitoring primary display 230. A single primary display 230 may display data from more than one computerized monitoring system. Alternately, primary display 230 may comprise two or more distinct screens, each of which may display data from one or more computerized monitoring systems.

When the centralized monitoring station 200 receives an alert from any of the computerized monitoring and communication systems 210A, 210B, 210C, indicating that a monitored person 110A, 110B, or 110C is making an audio request, audio, video, and/or alert information for that particular person may be displayed on the central monitoring alert display 250. An alert can be represented in one or more different types of physical configurations. It can be a visual cue on screen at the centralized monitoring station 200, such as the specific camera view flashing or being highlighted in a color to draw attention to that display among others. It can be an audible sound (e.g., a voice or alarm type sound) at the centralized monitoring station 200, an audible sound at the computerized monitoring system 210A, 210B, and 210C attached to the motion and/or sound sensors 120A, 120B, and 120C, a text message, an email, turning on a light or even running a program on a computer. Should the centralized monitoring station 200 receive alerts from more than one of the computerized monitoring and communication systems 210A, 210B, 210C, indicating that a person 110A, 110B, and/or 110C is making an audio request, the centralized monitoring alert display 250 may display the video, audio and/or alerting information from all such instances at the same time. If no alert is received by the centralized monitoring station 150, it may be that nothing is displayed on the centralized monitoring alert display 250. Preferably, all monitored individual rooms can be displayed and visible on the central monitoring primary display 230 whether alerting or not. When an alert is generated, attention can be drawn to the particular camera on central monitoring primary display 230 and/or a duplicative display of the alerting camera can be displayed on a second separate computer monitor, e.g., the centralized monitoring alert display 250.

An electronic record of any alerts received, any responses to the alert observed or received, and/or any actions taken by the centralized monitoring station 200 can be stored in a database 220.

Turning now to FIG. 4, the motion and/or sound sensors 400 is configured to monitor an area. The area includes a person 440 to be monitored along with an audio detection zone 430 surrounding the person 440 to be monitored. The audio detection zone 430 may be a predetermined distance around the person 440 to be monitored. The predetermined distance is customizable by the system owner or any user. The predetermined distance may vary per patient. For example, patients that are not very mobile or have difficulty moving may have a tighter or smaller audio detection zone (as they will not move around as much) than a patient that is very mobile or moves around a large amount (e.g., a child). Areas that are outside of the audio detection zone 430 but still within the area to be monitored are designated as audio ignore zones, such as audio ignore zone 410 and audio ignore zone 420. The audio in these zones may not be detected at all or may be detected but ignored (i.e., not analyzed to include keywords/commands).

Figure 5:
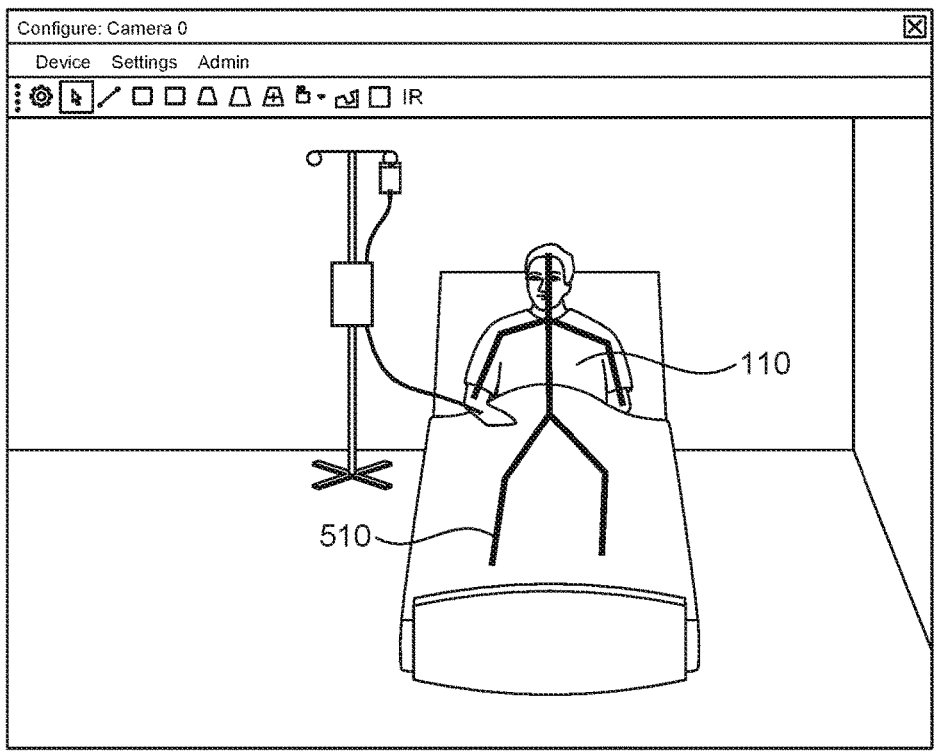
FIG. 5 is an exemplary configuration for an audio call detection system.
Figure 6:
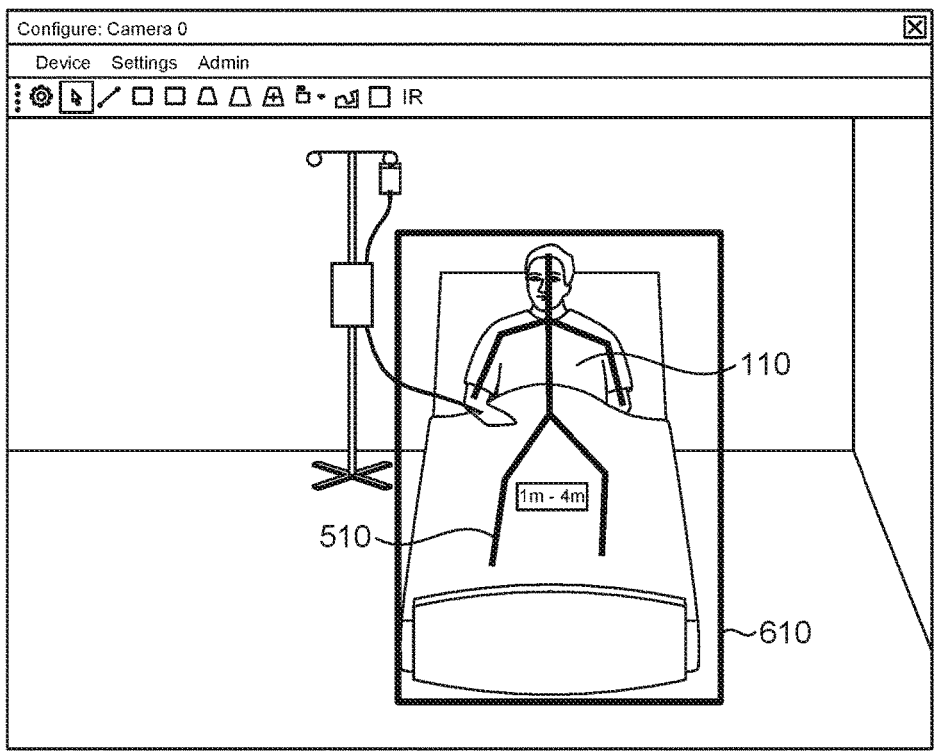
FIG. 6 is an exemplary configuration for an audio call detection system.

The motion and/or sound sensors (e.g., motion and/or sound sensors 120 of FIG. 2) may identify lines (to include curves) that likely correspond to human limbs and/or skeleton, shown as skeletal FIG. 510 in FIGS. 5 and 6. If an audio detection zone 610 has been established around a patient 110, a patient's bed, a patient's chair, or other support surface, a processor coupled to the 3D motion sensors 120 may identify skeletal FIG. 510 inside or primarily inside the audio detection zone 610 as the patient 110, and identify second or subsequent skeletal figures as others, such as caretakers or visitors. The skeletal FIG. 510 is shown in FIGS. 5 and 6 but alternate image analysis could be used, including, without limitation, blog recognition. No zones are marked in the image of FIG. 5. FIG. 6 illustrates, as previously mentioned, the audio detection zone 610, which could be configured in any way desired, as will be described below. In an embodiment, the audio detection zone is focused on a patient's mouth as this is where audio information will come from. In additional embodiments, the audio detection zone may also include the upper body of the patient to detect, for example, gestures. Hand gestures may be useful in identifying a patient call as well as movements. For example, a patient's movements may indicate that he/she is trying to get up. In this situation, the audio detection zone may move with the patient as the skeletal tracking indicates.

Customization of the audio detection zones may be configured by a user and may be applicable in either 2D or 3D environments. When configuring a 3D environment, for instance, a user may operate an input device to select a point on an image or video from the computerized monitoring station 130. The user may draw a perimeter defining a zone freehand, or may drag the input device (such as an electronic stylus or mouse pointer) from one point to another to define a diagonal axis for the perimeter of the zone. Other configuration options, including drag-and-drop templates and coordinate identification, could be used. Additionally, a user can configure the horizontal and vertical axes in a 2D environment to their desired specifications, as well.

Figure 7:
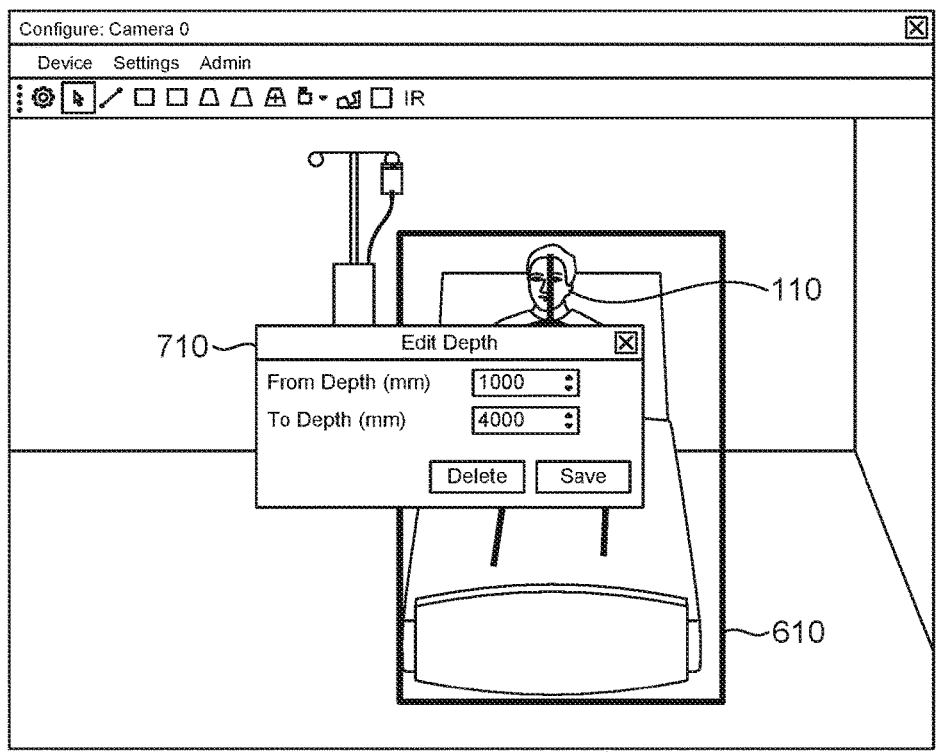
FIG. 7 is an exemplary configuration for an audio call detection system.

When applicable (i.e., in a 3D environment), the computerized monitoring system can define or recommend a depth measurement, or the user can provide the depth measurement. FIG. 7 provides a pop-up menu 710 allowing a user to configure or reconfigure the depth of a monitoring zone. The exemplary pop-up menu 710 solicits a depth parameter specified in millimeters (mm); however, any desired unit of measure could be used, including, without limitation, centimeters (cm), meters (m), inches, feet, and yards.

Alternatively or additionally, the patient 110 and/or caregiver 100 can be identified through the use of an electronic transmitter on the patient's or other individual's person. For example, the patient may wear a Bluetooth, infrared, RFID, or ultrasonic bracelet, tag, or button, or other identifying technology. Once a patient is identified, the software can automatically generate or allow the user to generate a configurable zone (e.g., 3D or 2D) or perimeter around the patient 110 and/or the patient's bed that acts as an audio detection zone 610.

In some aspects, the system may identify specific individuals, e.g., a particular patient 110 or a particular caregiver 100, using biometric identifiers such as facial recognition, height, distance between points on the body, etc. Alternately, or additionally, specific individuals may be identified by an electronic transmitter on the individual's person, such as an active or passive Bluetooth, infrared, RFID, ultrasonic, or other wired or wireless transmitter. The motion and/or sound sensors, or a separate sensor or array of sensors, could be used, for example, to read a barcode or encoded magnetic stripe on an identification badge worn by a caregiver 100 or patient 110. This functionality is optionally utilized to exclude individuals other than desired individuals from providing an audio request detected by the motion and/or sound sensors 120.

To ensure patient privacy and comfort, the system is configured such that monitoring may be turned on and off in its entirety, or only the audio feed may be turned on or off, or only the video feed may be turned on or off. The feeds are, thus, independently adjustable. If audio feeds are turned on, voice or word recognition algorithms may still run at the monitoring system even if the audio feed is disabled at a monitoring station. It may be desirable to disable audio and/or video feed to provide privacy to the person being monitored. For example, it may be desirable to disable audio and/or video feed while the person is being examined by a medical professional, or bathed, or while visitors are present. The need for detection of audio calls is somewhat reduced when the patient is interacting with medical professionals, caregivers, or visitors. However, if the audio and/or video feed is maintained when there are others present, there is a heightened need for the focused audio detection zones of the present invention.

The computerized monitoring system (such as computerized monitoring system 210A) may analyze only data related to the focused monitoring zones (i.e., audio detection zones), with or without capturing images and/or sound from a broader portion of the room. This may reduce total processing capacity required, as the most processing-intensive algorithms are run on a limited data set.

Figure 8:
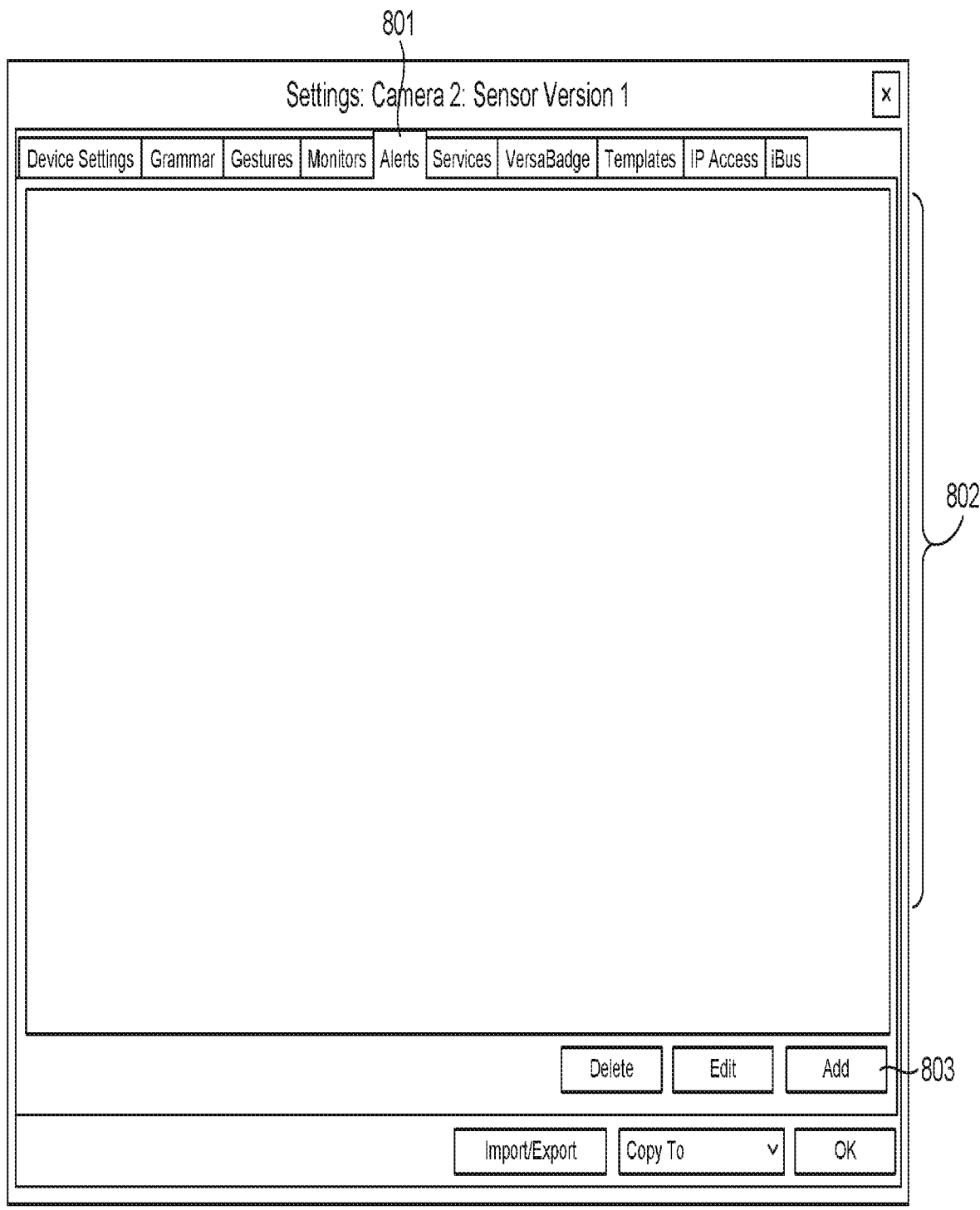
FIG. 8 is an exemplary configuration menu for an audio call detection system.
Figure 9:
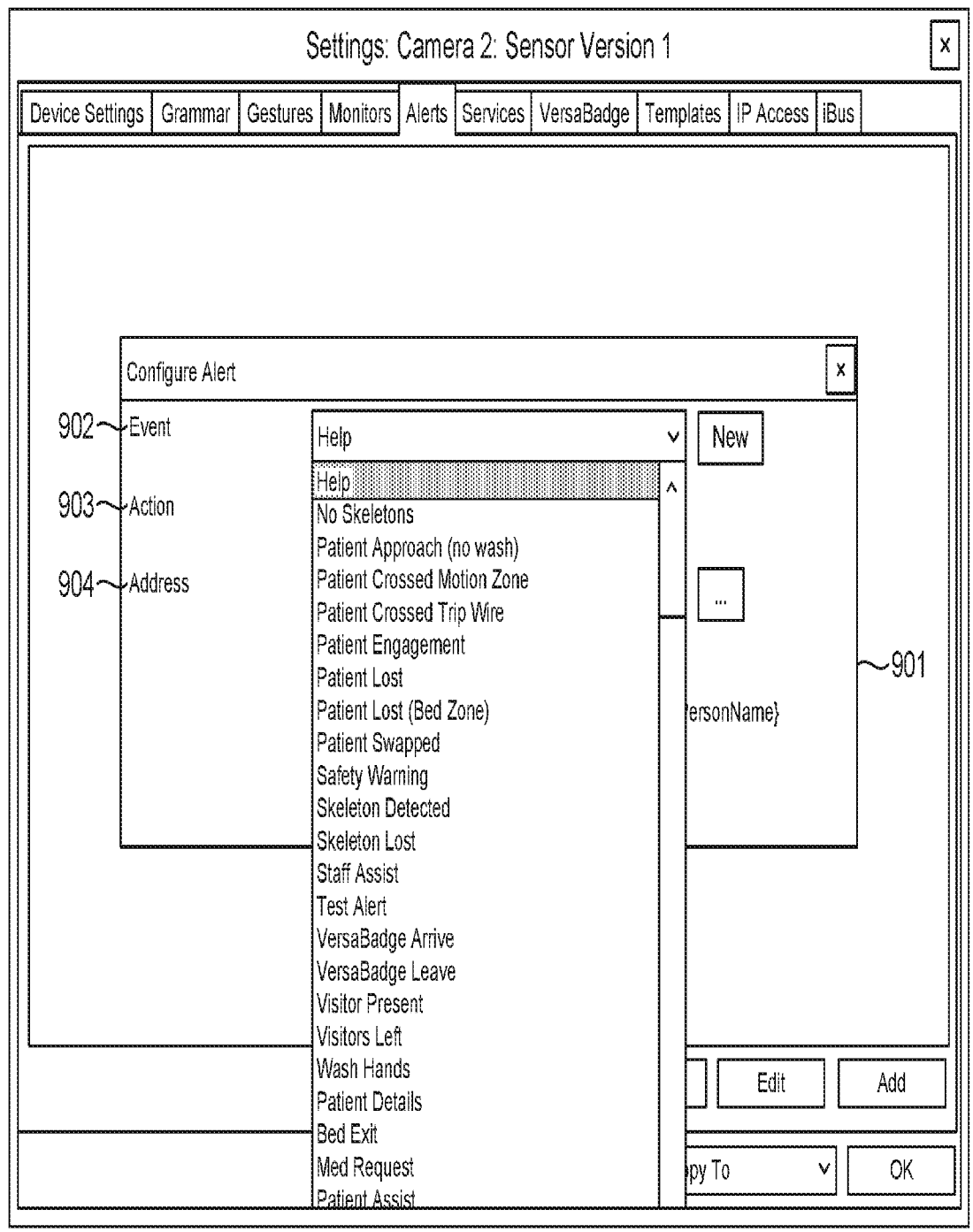
FIG. 9 is an exemplary configuration menu for an audio call detection system.

The system may be further configured with a variety of settings. FIG. 8 illustrates an exemplary configuration interface of configuration settings. FIG. 8 illustrates a selection of an alerts tab 801. The space 802 within the alerts window is blank, indicating that no alerts have been configured. If a user selects Add button 803 at the bottom of the alerts page, a new pop-up menu 901 may appear, as shown in FIG. 9. As shown in FIG. 9, pop-up menu 901 further includes drop-down menus to configure an alert by specifying an event 902, an action 903, and, if applicable, an address 904. As with the type of menus being customizable, the particular words used to describe an event, action, or address field may be modified to reflect the environment in which the system is being used, or the facility or personnel using the system or a particular station. For example, a system, station, or user interface may be configured for use in a hospital using clinical terminology. As another example, a remote central monitoring station may have an attendant who is not a medical professional, and lay terminology might be used in lieu of or in addition to medical terminology.

Initially, a user may select an event 902 from the drop-down menu. Exemplary events are provided in the drop-down menu and may vary across systems. For example, some events shown in the drop-down menu of FIG. 9 include skeleton lost (e.g., a skeletal figure of a patient has been lost, the patient got up perhaps), patient approach (no wash) (i.e., a caregiver is approaching a patient without having spent appropriate time at a wash station), etc.

Figure 10:
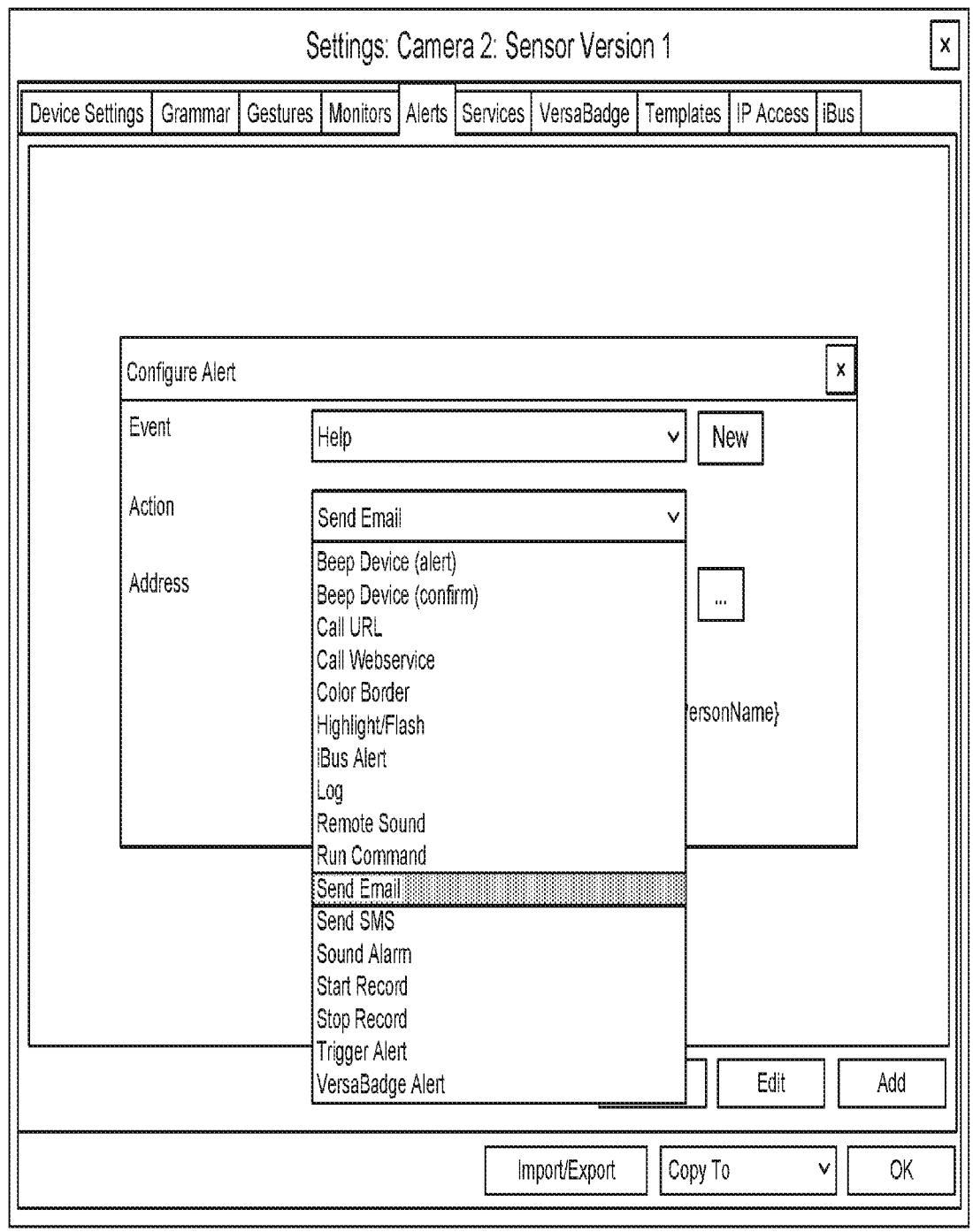
FIG. 10 is an exemplary configuration menu for an audio call detection system.
Figure 11:
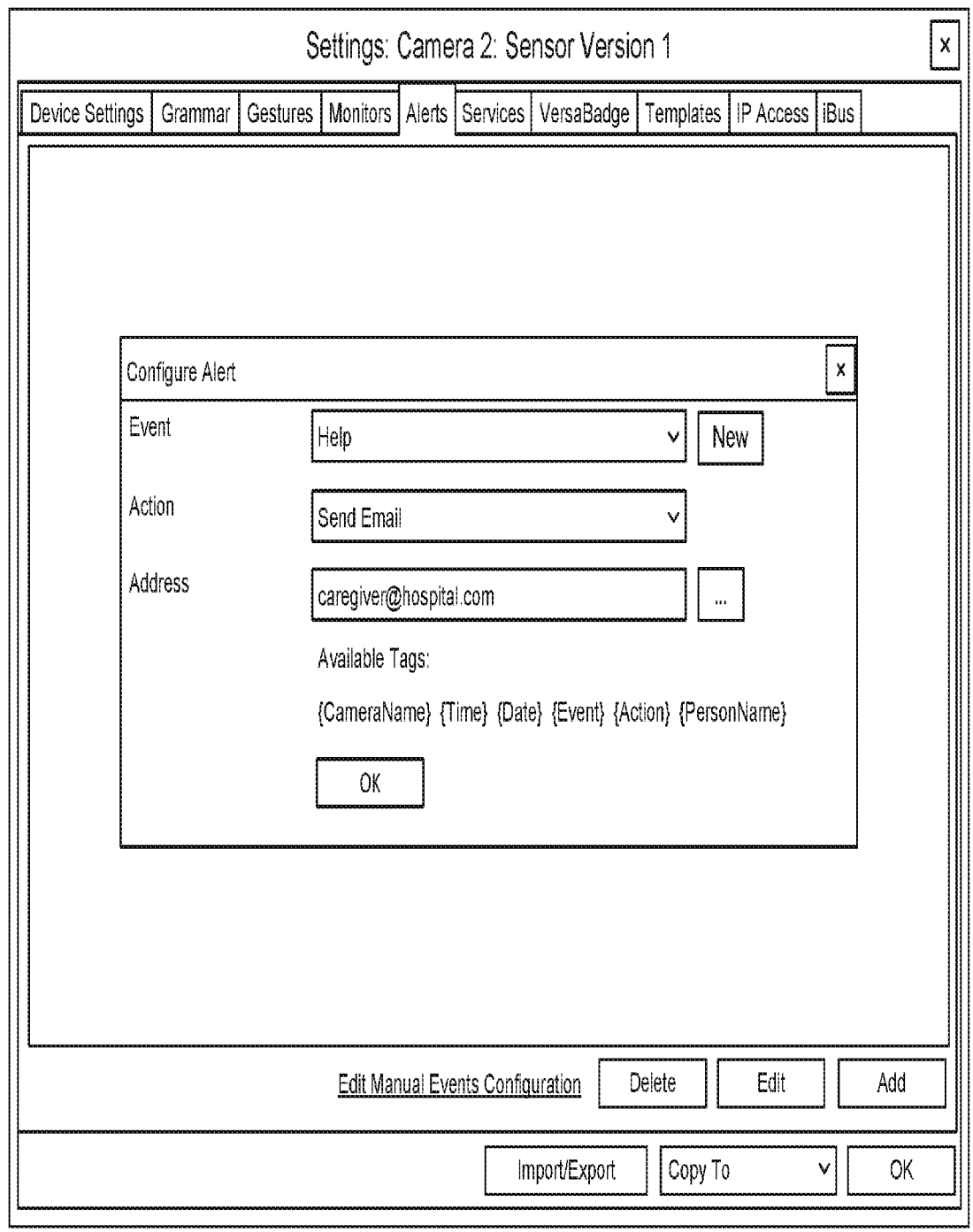
FIG. 11 is an exemplary configuration menu for an audio call detection system.
Figure 12:
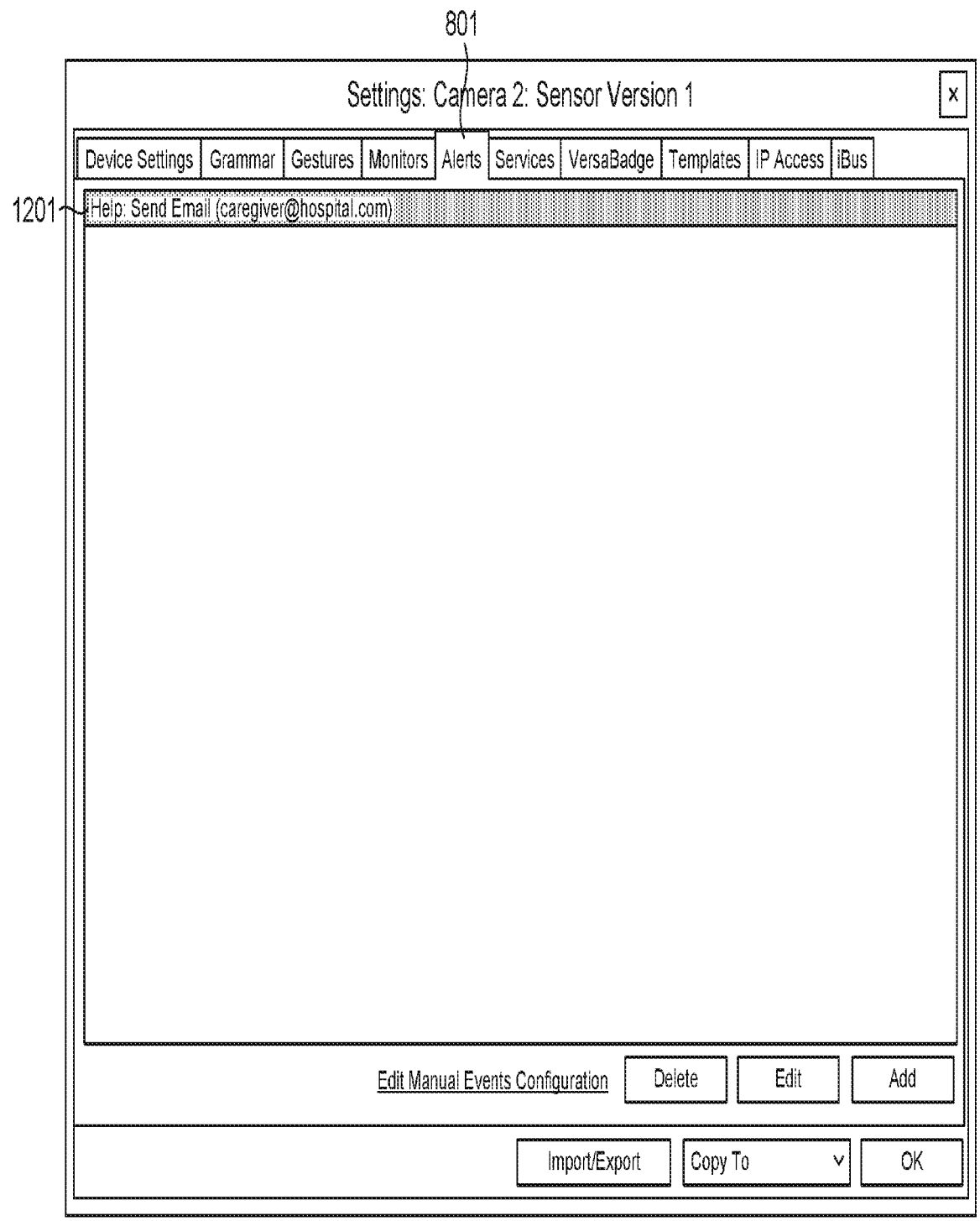
FIG. 12 is an exemplary configuration menu for an audio call detection system.

On selection of an event 902 in FIG. 9, the user may be able to select an action 903, shown in FIG. 10. Actions illustrate what to do when an event occurs. In FIG. 10, an exemplary event "Help" has been selected to configure. This may include an audio call for help. Actions that may be selected include, without limitation, sound alarm, trigger alert, beep device, etc. Several of the options relate to alerts, e.g., to provide different audible signals to the 3D sensors; to add or change a color border to display of image data; to highlight or flash a display of image data; to log an alert; to send an e-mail or SMS; or to provide other alerts. For illustration purposes only, the "send email" action is selected so that a user can enter an address at FIG. 11. The address may be for an individual (call nurse, attending clinician, etc.) or a group (e.g., pharmacy, cafeteria, nursing station, etc.). FIG. 12 illustrates that an alert 1201 is configured in the alerts tab 801. If additional alerts were configured, alerts window of FIG. 12 might display a selectable list of configured alerts. Once configured, alerts may be edited or deleted.

Figure 13:
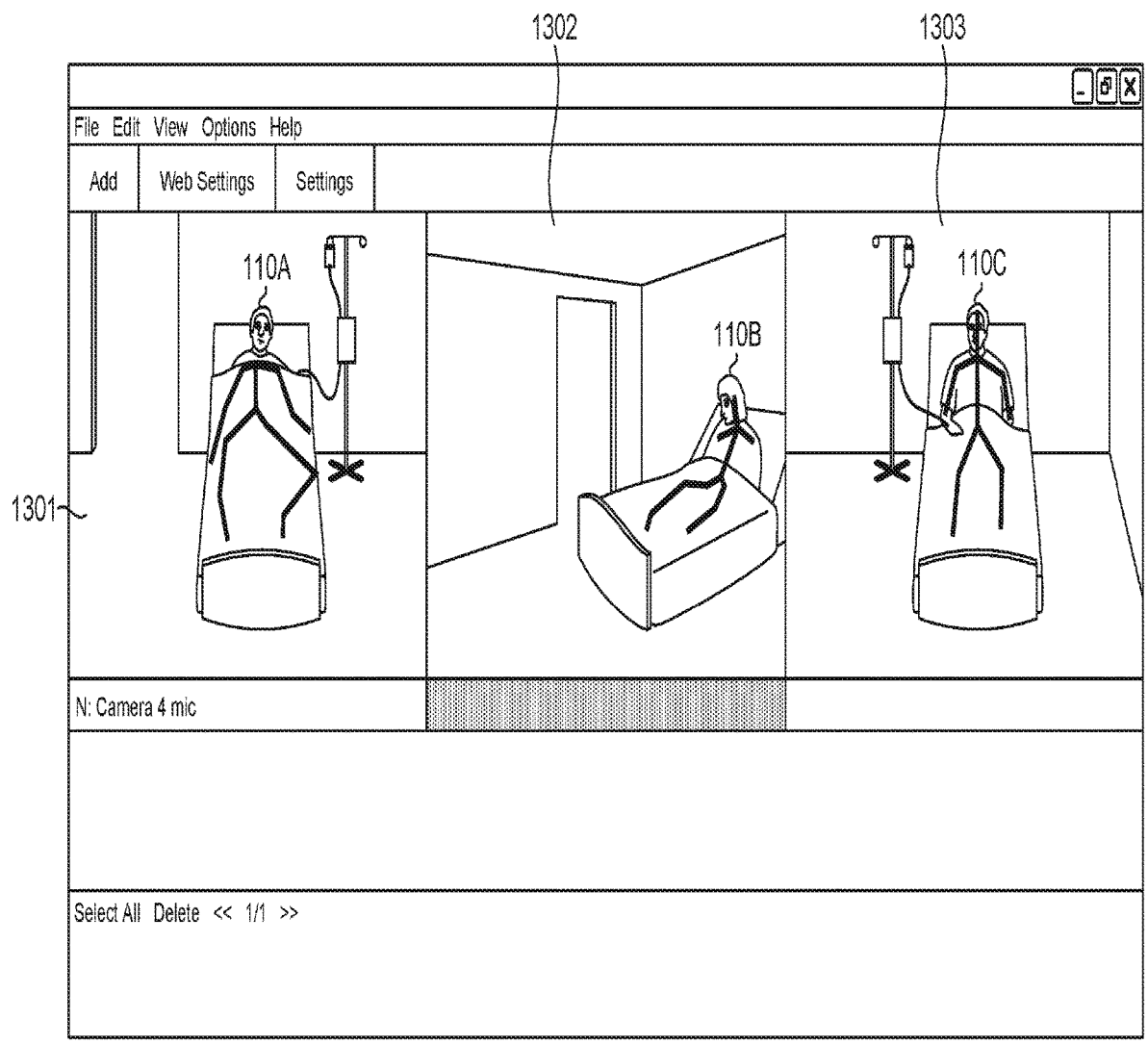
FIG. 13 is an exemplary display for an audio call detection system.

FIG. 13 provides a view of image data from multiple sensors monitoring persons 110A, 110B, and 110C, as might appear on a central monitor primary display 230. Depending on the configuration for primary display 230, each panel 1301, 1302, and 1303 may display live video, intermittent images (e.g., "still" shots from a video data feed), and/or audio data feed for monitored person 110A, 110B, and 110C, respectively. FIG. 13 also illustrates a difference in display panel 1302 as the bottom border of panel 1302 is shaded differently than the other panels 1301 and 1303. This may indicate an alert is present in that panel 1302. Different visual indicators may be used to show a graduated alert scale. For example, various colors may be used to indicate severity of alert, alert status (e.g., a clinician is responding to an alert, an alert has been sent to a clinician but not yet responded to, etc.), and the like.

As briefly mentioned herein, the system described may be utilized to monitor persons besides patients. For example, the system may be utilized as a staff command system where a caregiver's (or any other person besides the patient) voice is the one monitored and not the patient. This could be useful for identifying voice-activated requests for assistance (e.g., a caregiver calls for assistance with a patient), orders (e.g., a caregiver gives an order for a patient), and the like. This embodiment would operate as described as above with a focus on other persons than patients.

As is shown herein, the present invention provides a monitoring system that is able to monitor persons/patients to identify an audio call from the patient. The monitoring for audio calls may be focused to specific areas to reduce noise from other areas and to ignore audio from individuals other than patients. The present invention also intelligently routes detected audio calls (including one or more keywords/commands, phrases, etc.) to an appropriate role corresponding with the identified audio call (e.g., calls with keyword "magazine" may be routed to the gift shop; calls with keyword "food" may be routed to the cafeteria; calls with keyword "help" may be routed directly to the appropriate clinician, etc.).

In an alternate embodiment, the present invention provides a monitoring system that is able to monitor caregivers to identify audio instructions from the caregiver. The monitoring around caregivers is similar to that performed with respect to patients. For instance, an area within a predetermined distance from the caregiver may be monitored (audio detection zone) while other area (those including the patient, perhaps) are indicated as an audio ignore zone. As with patient audio calls, the present system can intelligently route audio inputs from a caregiver to the appropriate destination. For instance, if a caregiver orders that a different clinician visit the patient, the audio instruction may be routed to the different clinician.

Additionally, multiple audio detection zones may be utilized in the present invention. For example, an audio detection zone for the patient may be employed as well as an audio detection zone for a caregiver when the caregiver enters the room. Multiple audio detection zones may concurrently exist and each may be configured differently with respect to triggers identified within the zones. For instance, the configurable phrases, keywords, or commands that are triggers in a patient detection zone may be different from those that are identified as triggers within a caregiver detection zone.

From the foregoing, it will be seen that this disclosure is one well adapted to attain all the ends and objects hereinabove set forth together with other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. One or more non-transitory computer storage media storing computer-readable instructions that, when used by one or more computing devices, cause the one or more computing devices to perform operations comprising:

defining both an audio detection zone within a predetermined distance relative to a location of a first person to be monitored within a monitored environment and an audio ignore zone outside of the audio detection zone and within the monitored environment, wherein audio in the audio ignore zone is not identified, and wherein the location of the first person is identified using an identification apparatus configured to use skeletal figures, blob tracking, or facial tracking;

identifying audio detected in the audio detection zone by the first person; and providing an alert when the audio detected in the audio detection zone includes one or more inputs.

2. The computer storage media of claim 1, further comprising configuring a remote visual display to provide a live visual display of the motion data.

3. The computer storage media of claim 1, wherein the identification apparatus is further configured to identify and distinguish a voice of the first person from any other voice spoken using voice recognition.

4. The computer storage media of claim 1, wherein the identification apparatus is further configured to identify the location of the first person using an electronic transmitter on the first person's person, wherein the electronic transmitter is an active or passive Bluetooth, infrared, RFID, ultrasonic, or other wired or wireless transmitter.

5. The computer storage media of claim 1, further comprising logging the alert in a database.

6. The computer storage media of claim 5, wherein the database is configured to receive unknown inputs.

7. A method for monitoring patient calls, the method comprising:

identifying a patient in a monitored environment;

configuring an audio detection zone around the patient based on motion and sound data obtained from an identification apparatus configured to determine a location of the patient identified using skeletal figures, blob tracking, or facial tracking;

ignoring audio from any area outside of the audio detection zone, wherein audio is not identified from the area outside of the audio detection zone;

detecting one or more inputs originating from the audio detection zone; and generating an alert corresponding to the one or more inputs.

8. The method of claim 7, wherein the audio detection zone is an area that is a predefined distance around the patient to be monitored within the monitored environment, wherein the predefined distance includes one or more of a horizontal or vertical axes distance or a depth measurement.

9. The method of claim 7, further comprising identifying the area outside of the audio detection zone as audio ignore zones.

10. The method of claim 7, providing the alert to an appropriate role based on the one or more inputs.

11. The method of claim 7, wherein the alert is delivered to a monitoring apparatus physically remote from the room.

12. The method of claim 7, further wherein the audio detection zone moves with the location of the patient.

13. A method for monitoring caregiver calls, the method comprising:

identifying a location of an at least one caregiver using skeletal figures, blob tracking, or facial tracking for the at least one caregiver;

identifying an area surrounding the at least one caregiver as an audio detection zone based on the location of the at least one caregiver;

ignoring audio from any area other than the audio detection zone, wherein audio is not identified from the any area other than the audio detection zone; and monitoring the audio detection zone for one or more inputs spoken by the at least one caregiver within the audio detection zone.

14. The method of claim 13, further comprising providing an alert when the one or more inputs are detected within the audio detection zone.

15. The method of claim 13, wherein the audio detection zone is an area that is a predefined distance around the at least one caregiver, wherein the predefined distance includes one or more of a horizontal or vertical axes distance or a depth measurement.

16. The method of claim 13, further comprising monitoring movements of the skeletal figure.

17. The method of claim 13, further comprising identifying an area surrounding the patient as a second audio detection zone.

* * * * *